(12) United States Patent
Pischl et al.

(10) Patent No.: US 8,277,456 B2
(45) Date of Patent: Oct. 2, 2012

(54) SPINAL-COLUMN DISTRACTOR

(75) Inventors: Susanne Pischl, Ulm (DE); Thorsten Schmidt, Nersingen (DE); Nikolas Willmann, Ulm (DE)

(73) Assignee: Ulrich GmbH & Co. KG, Ulm (DE)

( * ) Notice: Subject to any disclaimer, the term of this patent is extended or adjusted under 35 U.S.C. 154(b) by 587 days.

(21) Appl. No.: 12/504,691

(22) Filed: Jul. 17, 2009

(65) Prior Publication Data

US 2011/0015638 A1    Jan. 20, 2011

(51) Int. Cl.
*A61B 17/58*    (2006.01)

(52) U.S. Cl. ......................................................... 606/90

(58) Field of Classification Search .................... 606/90, 606/105; 187/211; 254/10 C, 15, 16, 115
See application file for complete search history.

(56) References Cited

U.S. PATENT DOCUMENTS

| | | | | |
|---|---|---|---|---|
| 3,785,462 | A * | 1/1974 | Coad et al. | 187/262 |
| 5,193,649 | A * | 3/1993 | Lee | 187/244 |
| 6,582,451 | B1 * | 6/2003 | Marucci et al. | 606/207 |
| 6,840,944 | B2 * | 1/2005 | Suddaby | 606/105 |
| 7,625,377 | B2 * | 12/2009 | Veldhuizen et al. | 606/90 |
| 7,901,409 | B2 * | 3/2011 | Canaveral et al. | 606/86 R |
| 2006/0180403 | A1 * | 8/2006 | Hanlon | 187/269 |
| 2006/0235423 | A1 * | 10/2006 | Cantu | 606/90 |
| 2007/0260315 | A1 * | 11/2007 | Foley et al. | 623/17.12 |
| 2008/0114367 | A1 * | 5/2008 | Meyer | 606/90 |
| 2009/0222089 | A1 * | 9/2009 | Hauri et al. | 623/13.13 |
| 2010/0249791 | A1 * | 9/2010 | Roche | 606/90 |
| 2011/0001098 | A1 * | 1/2011 | Lee | 254/126 |

\* cited by examiner

*Primary Examiner* — Nicholas Woodall
(74) *Attorney, Agent, or Firm* — Andrew Wilford

(57) ABSTRACT

A spinal-column distractor (10) comprises a first pusher plate (1) intended to bear on a vertebra, a second pusher plate (2) intended to bear on an adjacent vertebra, and a slide (3). The slide (3) is connected to the first pusher plate (1) via a scissor linkage (4), and shiftable by a threaded spindle to change a spacing between the first pusher plate (1) and the second pusher plate (2), while the second pusher plate (2) forms a track for the slide (3).

13 Claims, 3 Drawing Sheets

SPINAL-COLUMN DISTRACTOR

FIELD OF THE INVENTION

The present invention relates to a spinal-column distractor, and in particular concerns a spinal-column distractor with a first pusher plate for bearing on a vertebra and a second pusher plate for bearing on an adjacent vertebra.

BACKGROUND OF THE INVENTION

Various spinal-column distractors are already known from the prior art. However, the disadvantage of previously known distractors is that a surgeon has difficulty handling them.

OBJECT OF THE INVENTION

Thus, the object of the invention is to develop a spinal-column distractor of the above-described type is easier to manipulate during surgery.

SUMMARY OF THE INVENTION

According to a first feature of the present invention this object of providing a spinal-column distractor with a first pusher plate intended to bear on a vertebra and a second pusher plate intended to bear on an adjacent vertebra is attained by connecting a slide to the first pusher plate via a scissor linkage, with the slide shiftable by a threaded spindle to change the spacing between the first pusher plate and the second pusher plate. The second pusher plate forms a track for the slide. This embodiment has the advantage that distraction of the vertebrae can be precisely adjusted in a simple manner.

Preferably, the threaded spindle comprises a coupling configured to connect with an insertion instrument. This makes it easier to operate the distractor by the insertion instrument. It proved to be advantageous for the coupling to have coupling notches that are embodied for engagement with teeth of the insertion instrument. It turned out to be particularly advantageous for the coupling notches to be formed as a multitooth coupling, particularly as a crown gear.

In a preferred illustrated embodiment of the distractor according to the present invention the first pusher plate has a bevel in an end facing away from and opposite the coupling. This facilitates the insertion of the distractor between the vertebral bodies of the spinal column.

Further, a groove to guide the holder of the insertion instrument may be formed on one longitudinal side of the distractor, particularly on both longitudinal sides of the second pusher plate, thereby increasing stability to stresses.

Moreover, the first pusher plate may be shaped to receive a spacer block intended to bear on a vertebra, so that the achievable distraction area can be flexibly adjusted by spacers of different heights.

The insertion instrument may further comprise a holder adapted to support the second pusher plate, thereby increasing stability. For better manageability the insertion instrument may further comprise a positioning rod.

According to a third feature of the present invention, for a distraction system this object is attained by a combination of one of the above-described distractors with one of the above-described insertion instruments.

BRIEF DESCRIPTION OF THE DRAWING

In the following the invention is explained in greater detail based on an illustrated embodiment shown in the drawing.

DETAILED DESCRIPTION

Figure 1:
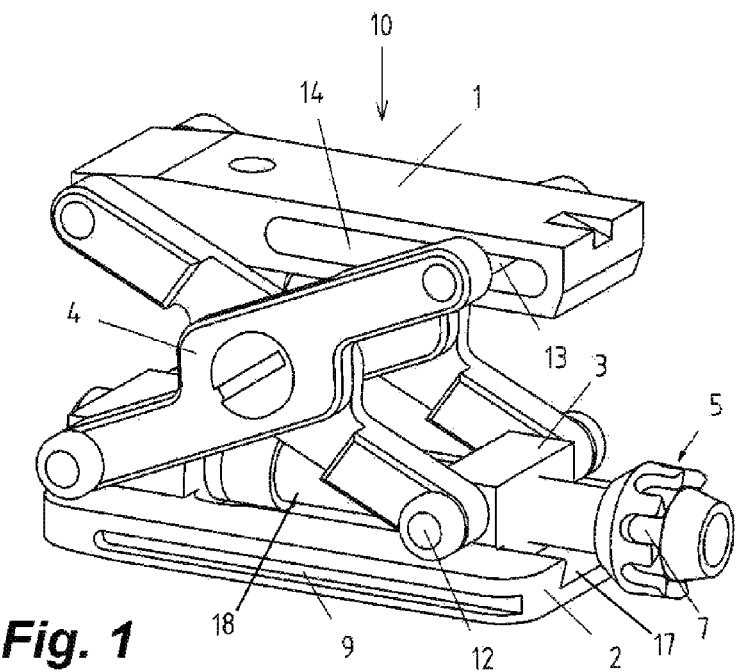
FIG. 1 is a schematic perspective view of a distractor according to the present invention.

FIG. 1 is a schematic perspective view of a spinal-column distractor 10. The distractor 10 comprises a first pusher plate 1 intended to bear on one vertebra, a second pusher plate 2 intended to bear on an adjacent vertebra, and a slide 3. The slide 3 is connected to the first pusher plate 1 via a scissor linkage 4 and can shift to change the spacing between the first pusher plate 1 and the second pusher plate 2 via a threaded spindle 18, with the second pusher plate 2 formed with a track 17 for the slide 3. This way, the distractor 10 can be distracted or shortened depending on the rotation direction.

The distractor 10 has a coupling 5 formed with coupling notches 7. The scissor linkage 4 may further comprise a guide rod 13 slidable in a guide slot 14 of the first pusher plate 1 when the scissor linkage 4 is moved. In addition, guiding slide 3 in a dovetail track 17 on the second pusher plate 2 can make a more even and gentler distraction possible. Here nuts 12 secure the slide 3 on the scissor linkage 4. The second pusher plate 2 may further be formed with a bevel 8 at the end facing away from and opposite the coupling 8.

Figure 2:
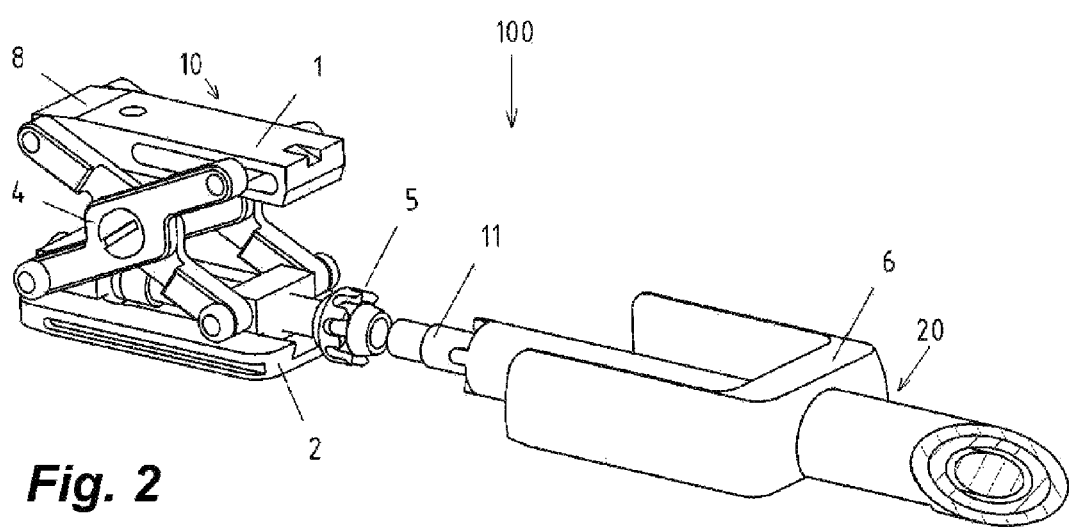
FIG. 2 is an illustration of the distractor from FIG. 1 coupled with an insertion instrument.

FIG. 2 schematically shows the connection of the distractor 10 with an insert instrument 20. For coupling, the distractor 10 is fitted to a holder 6 with the aid of a positioning rod 11. Engagement teeth of the insertion instrument 20 engage with the coupling notches 7 of the coupling 5 of the distractor 10. The distractor 10 can then be inserted into the intervertebral space by the holder 6. The insertion instrument 20 can carefully spread the distractor 10 until the desired distraction is achieved. By detaching the positioning rod 11 the holder 6 can be separated from the distractor 10, and the distractor 10 can remain in situ. After surgery the distractor 10 can be fitted to the holder 6 again and held by the positioning rod 11. By reverse rotating the insertion instrument 20 the distractor 10 can be shortened again, and thus removed from the intervertebral space.

Figure 3A:
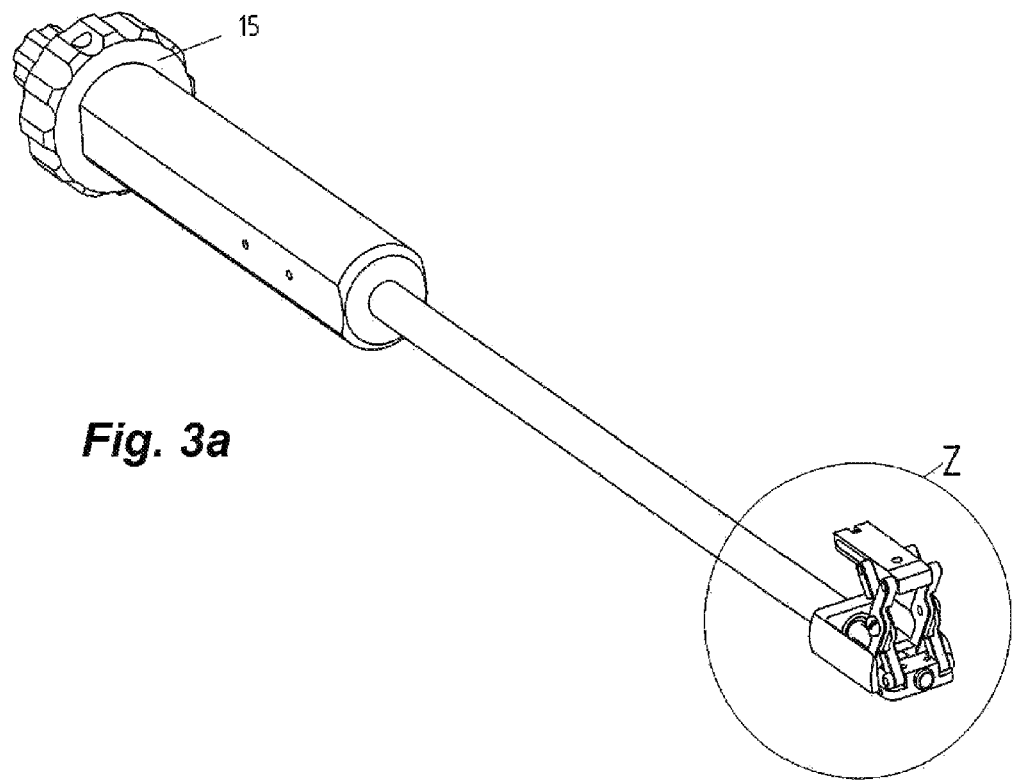
FIG. 3a is a schematic overview of a combination of the distractor with the insertion instrument according to the invention in a distraction position in which the pusher plates are at the furthest spacing from each other.

For a better understanding FIG. 3a shows a total overview of a distraction system 100 comprising the distractor 10 and the insertion instrument 20. A hand wheel 15 on the insertion instrument 20 serves for accurately controlling the distraction.

Figure 3B:
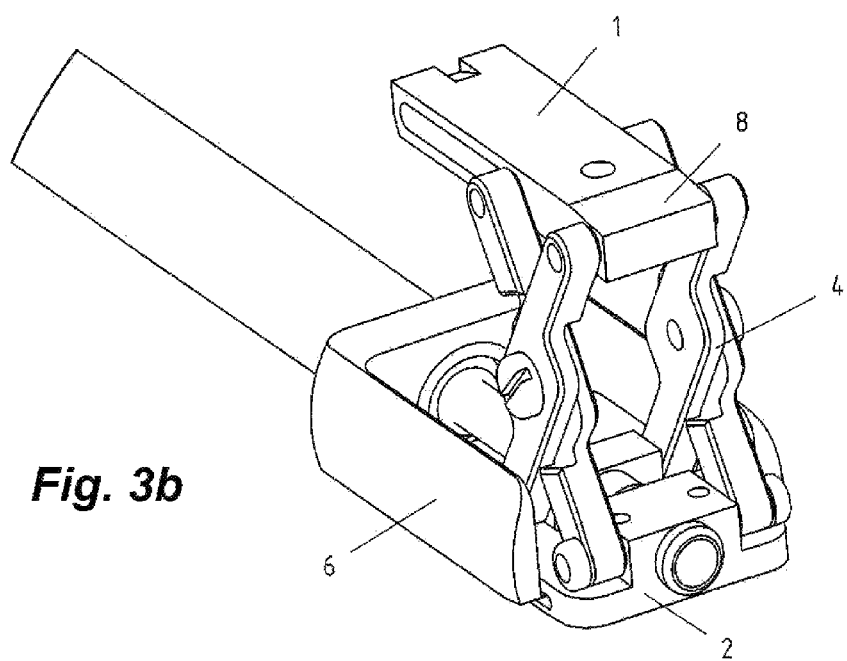
FIG. 3b is an enlarged view of the detail indicated at Z in FIG. 3a, and FIG. 4 is a perspective view like FIG. 1 of a variant of the invention.
Figure 4:
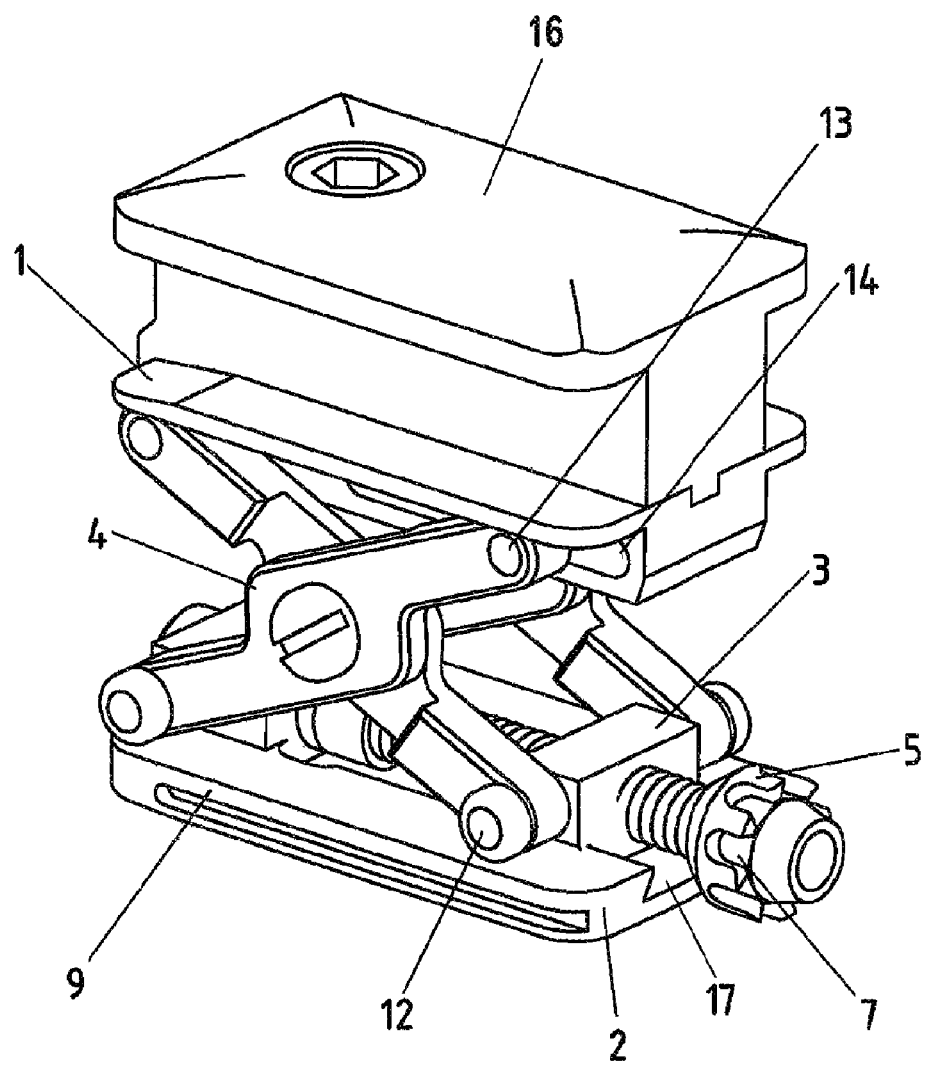

FIG. 3b shows a detailed and enlarged view of the Z detail of the distractor 10 from FIG. 3a, in which the first pusher plate 1 is at maximum spacing from the second pusher plate 2. To get a greater distraction, as shown in FIG. 4 attachments 16 of various heights can be mounted on the pusher plate 2.

The invention claimed is:

1. A spinal-column distractor comprising
a first pusher plate intended to bear on one vertebra,
a second pusher plate intended to bear on an adjacent vertebra and formed with a track,
a slide movable along the track,
a scissor linkage connecting the slide and the second pusher plate to the first pusher plate, and a threaded spindle connected to the slide and to the to second pusher plate for shifting the slide along the track on the second pusher plate to change a spacing between the first pusher plate and the second pusher plate.

2. The distractor in accordance with claim 1 wherein the threaded spindle is provided with a coupling constructed for connection with an insertion instrument.

3. The distractor in accordance with claim 2 wherein the coupling comprises coupling notches designed for engagement with teeth of the insertion instrument.

4. The distractor in accordance with claim 3 wherein the coupling notches form a multi-tooth coupling.

5. The distractor in accordance with claim 2 wherein the first pusher plate has a bevel in an end facing away from and opposite the coupling.

6. The distractor in accordance with claim 1 wherein the first pusher plate is shaped to receive a spacer block.

7. The distractor in accordance with claim 1 wherein the slide track is a dovetail groove.

8. The distractor in accordance with claim 1 wherein the first pusher plate has a guide slot to receive a guide rod of the slide.

9. An insertion instrument comprising
   a hollow shaft and
   a drive rod for coupling to a distractor in accordance with claim 1.

10. The insertion instrument in accordance with claim 9 wherein the insertion instrument comprises a holder shaped to hold the second pusher plate.

11. The insertion instrument in accordance with claim 9 wherein the insertion instrument comprises a positioning rod.

12. A combination of the distractor in accordance with claim 1 and an insertion instrument comprising:
   a hollow shaft and
   a drive rod for coupling to the distractor.

13. A spinal-column distractor comprising
   a first pusher plate intended to bear on one vertebra,
   a second pusher plate intended to bear on an adjacent vertebra and formed with a track and having sides each formed with a guide groove, the grooves being fittable with a holder of an insertion instrument,
   a slide movable along the track,
   a scissor linkage connecting the slide and the second pusher plate to the first pusher plate,
   a threaded spindle connected to the slide and to the second pusher plate for shifting the slide along the track on the second pusher plate to change a spacing between the first pusher plate and the second pusher plate, and
   a coupling constructed for connection with the insertion instrument.

* * * * *